United States Patent
Mondal et al.

(10) Patent No.: US 10,783,985 B2
(45) Date of Patent: *Sep. 22, 2020

(54) PHYSICS-BASED COMPUTATIONAL METHODS FOR PREDICTING COMPOUND SOLUBILITY

(71) Applicant: Schrödinger, LLC, New York, NY (US)

(72) Inventors: Sayan Mondal, New York, NY (US); Robert L. Abel, Brooklyn, NY (US)

(73) Assignee: Schrödinger, LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/267,085

(22) Filed: Feb. 4, 2019

(65) Prior Publication Data
US 2019/0237165 A1    Aug. 1, 2019

Related U.S. Application Data

(63) Continuation of application No. 15/142,178, filed on Apr. 29, 2016, now Pat. No. 10,216,911.

(Continued)

(51) Int. Cl.
*G06F 3/00* (2006.01)
*G16C 20/30* (2019.01)
*G06F 30/20* (2020.01)

(52) U.S. Cl.
CPC ............ *G16C 20/30* (2019.02); *G06F 30/20* (2020.01)

(58) Field of Classification Search
CPC ....................................................... G06F 19/16
(Continued)

(56) References Cited

U.S. PATENT DOCUMENTS 5,625,579 A    4/1997  Hinsberg, III et al.
8,170,806 B2 *  5/2012  Selifonov ............. G06N 3/126
                                                 702/19

(Continued)

FOREIGN PATENT DOCUMENTS

EP    2509015    10/2012
EP    2782033    9/2014
(Continued)

OTHER PUBLICATIONS

Keiichi Koyama, Field-Induced Martensitic Transformation in New Ferromagnetic Shape Memory Compound Mn1:07Co0:92Ge. (Year: 2004).*

(Continued)

*Primary Examiner* — Lechi Truong
(74) *Attorney, Agent, or Firm* — Fish & Richardson P.C.

(57) ABSTRACT

Methods of calculating a free energy of solubility for a compound in a solvent by computer operations include the following steps: (i) establishing, using a computer model, an initial state for a system including an aggregate of multiple molecules of the compound in a solvent; (ii) establishing, using the computer model, a final state of the system including a single molecule from the aggregate fully solvated in the solvent and separate from a transformed aggregate; (iii) transforming, using the computer model, the system from the initial state to the final state, via removing a first molecule of the compound from the aggregate to form the transformed aggregate and replacing the first molecule with solvent at the site of the first molecule; and (iv) calculating the free energy of the transformation between the initial and the final states, which determines the free energy of solubility for the compound.

21 Claims, 5 Drawing Sheets

Related U.S. Application Data

(60) Provisional application No. 62/155,770, filed on May 1, 2015.

(58) Field of Classification Search
USPC .......................................................... 703/11
See application file for complete search history.

(56) References Cited

U.S. PATENT DOCUMENTS

| | | | |
|---|---|---|---|
| 10,216,911 B2 | 2/2019 | Mondal et al. | |
| 2003/0228624 A1* | 12/2003 | Diller ................ | C07K 1/047 435/7.1 |
| 2004/0225451 A1 | 11/2004 | Filikov | |
| 2008/0147360 A1 | 6/2008 | Fejes et al. | |
| 2012/0116742 A1 | 5/2012 | Prakash et al. | |
| 2015/0095007 A1 | 4/2015 | Mackerell et al. | |
| 2015/0317459 A1* | 11/2015 | Farhi ................ | G06F 17/10 703/2 |
| 2016/0321432 A1 | 11/2016 | Mondal | |

FOREIGN PATENT DOCUMENTS

| | | |
|---|---|---|
| JP | 2003536117 | 12/2003 |
| JP | 2009080803 | 4/2009 |
| WO | 1998054665 | 12/1998 |
| WO | 2005038429 | 4/2005 |
| WO | 2011016743 | 2/2011 |
| WO | 2014091480 | 6/2014 |

OTHER PUBLICATIONS

Extended European Search Report in Application No. 16789816.2, dated Jun. 13, 2018, 16 pages.

International Preliminary Report on Patentability in International Application No. PCT/US2016/030022, dated Nov. 7, 2017, 7 pages (with English translation).

International Search Report and Written Opinion; PCT/US2016/30022; dated Dec. 16, 2016; 18 pages.

Karandu et al., "Solubility and Aggregation of Gly 5 in Water", Journal of Physical Chem. Part B: Condensed Matter Materials Surface, vol. 118, No. 32, Jul. 30, 2014, pp. 9565-9572.

Kollman, P. "Free Energy Calculations: Applications to Chemical and Biochemical Phenomena," Year 1993.

Levy et al., "On the Nonpolar Hydration Free Energy of Proteins: Surface Area and Continuum Solvent Models for the Solute-Solvent Interaction Energy", J. Am. Chem. Soc, 2003, 125, p. 9523-9530; the entire document.

Shivakumar et al., "Prediction of Absolute Solvation Free Energies using Molecular Dynamics Free Energy Perturbation and the OPLS Force Field", Journal of Chem. Theory and Computation: JCTC, vol. 6, No. 5, May 11, 2010, pp. 1509-1519.

Skyner et al., "A review of methods for the calculation of solution free energies and the modelling of systems in solution", Physical Chemistry Chemical Physics., vol. 17, No. 9, Jan. 1, 2015, pp. 6174-6191.

Tjong et al., "Prediction of Protein Solubility from Calculation of Transfer Free Energy", Biophysical Journal, vol. 95, No. 6, Sep. 2008, pp. 2601-2609.

Wallqvist et al., "Molecular Dynamics Study of the Dependence of Water Solvation Free Energy on Solute Curvature and Surface Area", J. Phys. Chem. 1995, 99, p. 2885-2892; p. 2890, col. 2, para 1; p. 2891; abstract.

Wang et al., "Absolute Binding Free Energy Calculations Using Molecular Dynamics Simulations with Restraining Potentials", Biophysical Journal, vol. 91, No. 8, Oct. 1, 2006, pp. 2798-2814.

EP Office Action in European Appln. 16789816.2-1111, dated Jun. 13, 2019, 5 pages.

JP Office Action in Japanese Appln. 2017-556216, dated Apr. 1, 2020, 9 pages (with English translation).

* cited by examiner

```
         ┌─────────────────────────────────────────────┐
         │     Establish an initial state for a system │
  210 ── │ comprising an aggregate of multiple molecules│
         │         of the compound in a solvent        │
         └─────────────────────────────────────────────┘
                              │
                              ▼
         ┌─────────────────────────────────────────────┐
         │       Establish a final state for the system│
  220 ── │    comprising a single molecule from the    │
         │    aggregate fully solvated in the solvent and│
         │      separate from the remaining aggregate  │
         └─────────────────────────────────────────────┘
                              │
                              ▼
         ┌─────────────────────────────────────────────┐
         │  Transform the system from the first state to│
         │ the final state by removing a first molecule of│
  230 ── │   the compound from the aggregate and       │
         │ replacing the first molecule with solvent at the│
         │           site of the first molecule        │
         └─────────────────────────────────────────────┘
                              │
                              ▼
         ┌─────────────────────────────────────────────┐
         │       Calculate the free energy of the      │
  240 ── │   transformation between the initial and the│
         │ final states based on a free energy of the initial│
         │   state and a free energy of the final state│
         └─────────────────────────────────────────────┘
```

PHYSICS-BASED COMPUTATIONAL METHODS FOR PREDICTING COMPOUND SOLUBILITY

CROSS-REFERENCE TO RELATED APPLICATION

This application is a continuation application of U.S. application Ser. No. 15/142,178, filed on Apr. 29, 2016, which claimed priority to U.S. Application Ser. No. 62/155,770 filed on May 1, 2015, which is incorporated herein by reference.

TECHNICAL FIELD

This invention relates to computational methods for predicting whether a compound is soluble in a solvent.

BACKGROUND

Solubility is an important characteristic in assessing a compound's suitability for various applications, including pharmaceutical, environmental, and industrial application. For example, water solubility is an important characteristic for orally-administered pharmaceutical compounds. Typically, empirical methods are used to determine a compound's solubility but these can be an expensive, time-consuming task, particularly, e.g., in the lead optimization phase of a drug discovery project where a multitude of structural and chemical variants of a new molecular entity (NME) are possible.

Today, computational simulations are used to assist solving a variety of chemical and biochemical problems, such as in computer-aided drug design where computational simulations are used to predict, e.g., whether a given molecule will bind to a target and if so how strongly. A reliable, accurate computational method for predicting compound solubility would be a desirable alternative or complement to conventional empirical approaches. In addition, the ability of the method to provide a structural explanation for the predicted solubility of a compound may facilitate the design of variants with improved solubility.

SUMMARY

Computational methods for predicting whether a compound is soluble in a solvent are disclosed. When considering a computer model of a solid aggregate of the compound in a solvent bath, accurate predictions may be made tractable by calculating a free energy of solubility for the compound as the sum of the free energy of sublimation of a single molecule of the compound from the aggregate to vacuum and the free energy of solvation of a molecule into the solvent bath.

Sublimation may occur via alchemical or physical removal of the molecule from the aggregate. The sublimation may be performed with the aggregate surrounded by a fast diffusing solvent, i.e., such that solvent molecules replace the sublimated molecule without re-equilibrating the system of aggregate, as it would otherwise take a long time for the hole to be filled by thermal fluctuation of the pure solid. The relaxation times of liquids are often on the order of or faster than the time scale of the simulation, which allows for accurate calculation of sublimation free energy in a computationally efficient manner. Generally, the sublimated molecule is selected from the interface of the aggregate and the solvent. Solvation occurs by introducing a molecule of the compound into the solvent bath.

These calculations may be advantageously used in rational drug design, optimization, and formulation where, e.g., water soluble compounds are desired for pharmaceutical use. Such analyses may also aid in the selection of co-solvents/excipients to enhance the aqueous solubility of drug candidate molecules during the formulation process.

In general, in a first aspect, the invention features methods that include calculating a free energy of solubility for a compound in a solvent by computer operations which include the following steps: (i) establishing, using a computer model, an initial state for a system including an aggregate of multiple molecules of the compound in a solvent; (ii) establishing, using the computer model, a final state of the system including a single molecule from the aggregate fully solvated in the solvent and separate from a transformed aggregate; (iii) transforming, using the computer model, the system from the initial state to the final state, via removing a first molecule of the compound from the aggregate to form the transformed aggregate and replacing the first molecule with solvent at the site of the first molecule; and (iv) calculating the free energy of the transformation between the initial and the final states, which determines the free energy of solubility for the compound.

Implementations of the methods can include one or more of the following features. For example, the aggregate can be an amorphous solid, a crystal, or a super-cooled liquid.

The transformation can include the steps of: (i) removing a first molecule of the compound from the aggregate to vacuum, and replacing the first molecule with solvent at the site of the first molecule; and (ii) introducing a second molecule of the compound into the solvent so that the second molecule is fully solvated in the solvent.

The free energies can be calculated via free energy perturbation, thermodynamic integration, by determining a potential of mean force, by Bennett acceptance ratio (BAR) method, and/or by Zwanzig averaging.

The first unit can be located at an interface between the aggregate and the solvent.

Calculating the free energy of solubility for the compound may include repeating steps (ii), (iii) and (iv) for molecules from multiple different sites, and calculating an average of the free energy of initial and final states of the system for the multiple different sites.

In some embodiments, establishing the initial system includes equilibrating the aggregate and then introducing the aggregate into the solvent and equilibrating the aggregate in the solvent.

The system can be simulated using Molecular Dynamics and/or Monte Carlo simulations.

The solvent may be water. The compound may be a small molecule. In some embodiments, the small molecule is a candidate molecule for a pharmaceutical application.

The method can include designing a new compound based on visualizing the aggregate in the solvent.

In general, in a further aspect, the invention features methods for identifying soluble compounds, including visualizing, using a computer model, an aggregate including multiple units of an initial compound in a solvent, the initial compound being insoluble in the solvent; identifying molecular features of the initial compound that reduces its solubility based on the visualization of the aggregate in the solvent; establishing a plurality of different candidate compounds based on the visualization of the initial compound, the structure of each of the candidate compounds being variants of the initial compound; using a method of the first aspect of the invention to determine a free energy of solubility of each of the candidate compounds; selecting one or more of the candidate compounds for synthesis based on the determined free energy of solubility of each of the candidate compounds; and measuring an actual solubility of each of the synthesized candidate compounds and identifying which of the synthesized candidate compounds are soluble in the solvent.

In general, in another aspect, the invention features methods for identifying soluble compounds, including: visualizing, using a computer model, an aggregate including multiple units of an initial compound in a solvent, the initial compound being insoluble in the solvent; identifying molecular features of the initial compound that reduces its solubility based on the visualization of the aggregate in the solvent; establishing a plurality of different candidate compounds based on the visualization of the initial compound, the structure of each of the candidate compounds being variants of the initial compound; for each of the candidate compounds, determining a free energy of solubility by calculating a free energy for a first state of the system and a second state of the system, the first state of the system corresponding to removing a first unit of the compound from the aggregate and replacing the first unit with solvent at the site of the first unit, and the second state of the system corresponding to introducing a second unit of the compound into the solvent so that the second unit is fully solvated in the solvent; selecting one or more of the candidate compounds for synthesis based on the determined free energy of solubility of each of the candidate compounds; and measuring an actual solubility of each of the synthesized candidate compounds.

The method can include identifying at least one of the synthesized candidate compounds for development, e.g., as a candidate for a pharmaceutical application or some other application.

The details of one or more embodiments are set forth in the accompanying drawings and the description below. Other features and advantages will be apparent from the description and drawings, and from the claims.

DESCRIPTION OF DRAWINGS

FIG. 2 is a flow chart showing steps in an exemplary method for calculating the free energy of solubility of a compound.

Like reference symbols in the various drawings indicate like elements.

DETAILED DESCRIPTION

Equilibrium Solubility refers to a compound's equilibrium concentration (typically in mol/L or mg/L) in a solution in contact with an excess of the compound in a solid state. The physical process reaches equilibrium when the rate of compound molecules joining the solid state from solution equals the rate of compound molecules leaving the solid to be solvated. Kinetic Solubility, which is often the solubility measured in empirical studies, is the concentration of a compound in solution when an induced precipitate first appears.

Solubility free energy, $\Delta G_{solubility}^{\circ}$, is a thermodynamic property indicative of the energy change associated with the dissolution of a substance in a solvent. Solubility free energy, typically provided in units of kcal/mol, provides valuable insight into the solubility of a compound because it is indicative of whether, and by how much, dissolution of the compound into the solvent is energetically favorable or unfavorable.

Solubility (S) in units of mol/L may be calculated from:

$$S = \exp[(-\Delta G_{solubility}^{\circ})/k_B T]$$

where $k_B$ is the Boltzmann constant, and T is the temperature.

Figure 1:
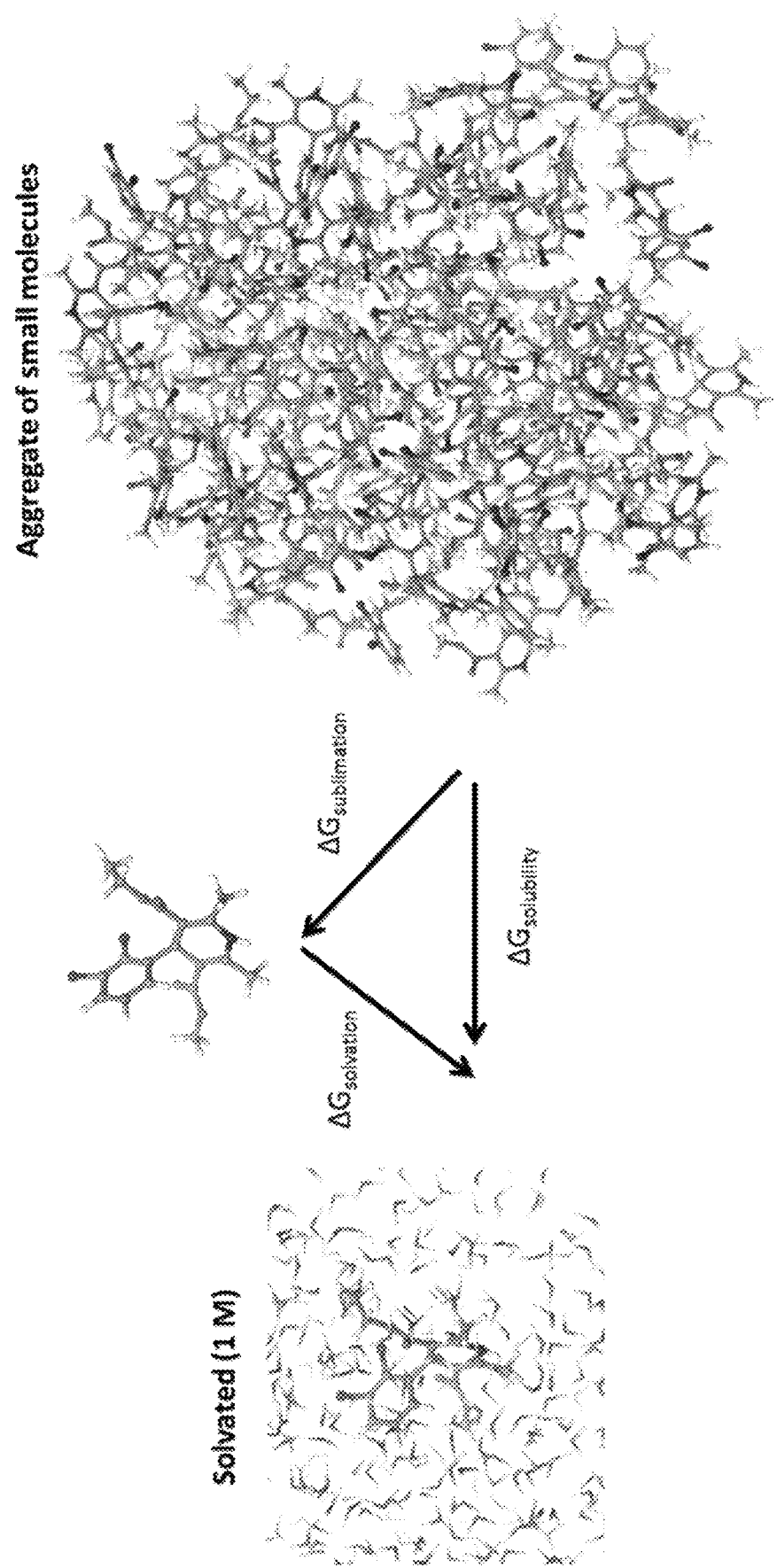
FIG. 1 is a diagram illustrating a thermodynamic cycle for an aggregate of amorphous felodipine where the solubility free energy is decomposed into the sum of the sublimation free energy and the solvation free energy.

Referring to FIG. 1, one approach to calculating the solubility free energy of a system is to decompose $\Delta G_{solubility}^{\circ}$ into the sum of the sublimation free energy ($\Delta G_{sub}^{\circ}$) and the solvation free energy ($\Delta G_{solv}^{\circ}$), i.e., $$\Delta G_{solubility}^{\circ} = \Delta G_{sub}^{\circ} + \Delta G_{solv}^{\circ}.$$

For a system composed of an aggregate (e.g., a solid aggregate) of multiple molecules of the compound, the sublimation free energy refers to the change in the free energy of the system that occurs upon removal to vacuum of a single molecule of the compound from a solid aggregate of the compound.

The sublimation and solvation free energies can be determined by computer simulation of the aggregate/solvent system. Computational simulation of molecular interactions have long been used to determine properties of molecules including molecular structure, energies, charge distributions, reactivities, etc.

In general, a variety of computational techniques may be used in order to determine the sublimation, solvation, and solubility free energies. These techniques include without limitation free energy perturbation (FEP), thermodynamic integration (TI), Bennet Acceptance Ratio (BAR), determination of the potential of mean force, weighted histogram analysis methods (WHAM), and Zwanzig averaging. Likewise the requisite data for the application of these free energy estimators might be computed via molecular dynamics (MD) and Monte Carlo (MC) simulations.

In some embodiments, combinations of computational techniques can be used for different portions of the calculations. For example, the system can be equilibrated using one technique, while the free energies are calculated using a different technique. For instance, as is the case in the example described below, the system can be equilibrated using MD and, after equilibration, the free energies may be determined using FEP.

The aggregate is established by placing, in a spatial coordinate system established by the computer model, a number of molecules of the compound in relatively close proximity to one another and placing the molecules under appropriate pressure (e.g., atmospheric pressure) and temperature (e.g., room temperature or body temperature).

A variety of intramolecular and intermolecular interaction models may be incorporated into a computer model of the system. In general, the molecules composing the aggregate are bound to each other by Van der Waals and electrostatic forces, and other interactions (e.g., ionic or covalent bonding) are not necessary (but may be included if desired).

The process of removing the molecule from the aggregate may be an alchemical process, which means that the process is non-physical.

When selecting molecules for the sublimation free energy calculation, molecules that are at the interface of the aggregate and solvent are selected for alchemical annihilation. A variety of techniques can be used to select appropriate molecules for sublimation. In some embodiments, the sites can be selected by visualization and manual selection. Visualization can be performed using commercially-available software, such as Maestro and PyMOL (both available from Schrödinger, New York, N.Y.), or Visual Molecular Dynamics (VMD) (originally developed by the University of Illinois and the Beckman Institute). Visualization allows a user to view the structure of the aggregate and identify those molecules that are at the surface of the aggregate. Alternatively, or additionally, an algorithm can be used to select molecules for sublimation. For example, an algorithm can be used to calculate the solvent exposure of heavy atoms (i.e., non-hydrogen atoms) and make a selection based on either which molecules have the highest solvent exposure and/or which molecules have at least a threshold amount of solvent exposure. Algorithms may be used which determine solvent exposure based on geometric considerations. Algorithms using Solvent-Accessible Surface Area (SASA) techniques are examples that may be used.

For purposes of the calculation, a "fast diffusing" solvent is used so that it rapidly fills the spaces created by the molecule annihilated in the sublimation step. This can be achieved by choosing a solvent with a relaxation time on the order or faster than the time scale of the simulation, which allows one to avoid the long-time scale rearrangement of the aggregate that would be required for the system of aggregate to re-equilibrate after the alchemical annihilation of the molecule. It is widely known that many solvents are fast diffusing at room temperature and pressure, notably water at room temperature or body temperature, which facilitates the formulation of a computationally efficient approach.

The solvation free energy refers to the change in free energy of solvating from vacuum a single molecule of the compound in solution in the system. Rather than calculating $\Delta G_{solubility}^{\circ}$ directly, e.g., by evolving a model system by molecular dynamics, the above equation indicates that $\Delta G_{solubility}^{\circ}$ can be calculated by separately calculating $\Delta G_{sub}^{\circ}$ and $\Delta G_{solv}^{\circ}$ and determining the solubility free energy as their sum.

In certain embodiments, the solid aggregate is an amorphous aggregate. This means that there is no long range orientational or translational ordering between the molecules forming the aggregate. Amorphous aggregates are relatively simple to model computationally. One can do so by specifying a number of molecules of the compound in relatively close proximity to one another and simulating them under appropriate conditions of pressure and temperature (e.g., using an annealing approach). To achieve improved sampling in obtaining the amorphous aggregate, enhanced sampling methods like simulated annealing may be used. Conversely, crystalline aggregates may be computationally challenging to achieve because the precise crystalline form is difficult to predict. Moreover, many empirical studies involve amorphous aggregates, so it is expected that computational simulations done with amorphous aggregates can provide accurate predictions for such empirical studies. For example, calculations based on amorphous aggregates are believed to accurately estimate empirical studies because in kinetic measurements of solubility, e.g., widely used in drug discovery programs, compounds are predominantly in an amorphous state. Kinetic solubility refers to a compound's solubility in a metastable state (rather than thermodynamic) and is a common measurement type used in the optimization phase of lead compounds in drug studies. Moreover, it is believed that even in measurements of "thermodynamic solubility" often reported in the literature, many of the solids investigated may contain significant amorphous impurities. Moreover, some drugs are formulated as amorphous material to facilitate dissolution.

While amorphous aggregates may be advantageous, the methods disclosed herein are not so limited and other solid forms are also possible. For example, in some embodiments, the aggregate may be crystalline. Crystalline aggregates have both long range orientational order and long range translational order between the molecules forming the aggregate. Intermediately ordered aggregates are also possible. For example, in some embodiments, the aggregate is quasi-crystalline or liquid crystalline.

In general, either or both the sublimation and solvation free energies may be calculated from a single instance of the system or from multiple replicates. For example, the sublimation free energy may be determined by calculating a free energy of an alchemical annihilation of a different molecule from each of several replicates of the system, and averaging the multiple values to determine the sublimation free energy. Any number of replicates may be used. For example, two to ten replicates may be used (e.g., five or six replicates). In some cases, a larger number of replicates may be used (e.g., about 15, about 20, about 30 or more). Generally, the number of replicates will depend on computational expense.

Calculations using multiple replicates may also be used to check for convergence of the calculated solubility. In other words, the calculated solubility free energy for different subsets of replicates can be compared to ensure that each is within an acceptable range of the average value. Lack of convergence may be used to eliminate or discount computational information about a specific compound.

In many instances, the solvent of interest is water. However, in general, the calculation methods can be used for a variety of solvents. For example, organic solvents, such as alcohol acetone, chloroform, toluene, DMSO, ethanol, propylene glycol, dimethyl acetamide may be used, with several of these being important for formulating drug candidates with poor aqueous solubility. In some embodiments, the solvent is an aphysical solvent, i.e., a computational solvent not corresponding to any physical solvent. For example, a solvent having non-integral charge can be used.

Furthermore, a variety of compounds may be investigated using these calculation methods. In many instances, the compound is an organic compound, such as an organic small molecule (e.g., a molecule with a relatively low molecular weight, such as <900 daltons, that may help regulate a biological process). The small molecule may be a candidate molecule for a pharmaceutical application.

Examples of compounds include clotrimazole, clozapine, felopidine, indomethacin, ketoconazole, efavirenz, ritonavir, and loratadine.

FIG. 2 shows, in the form of a flow chart, an exemplary method (200) for calculating the free energy of solubility for a compound in water.

The first step (step 210) involves establishing an initial state for a system composed of the aggregate of the compound in water. This involves first defining the structure of the aggregate (i.e., the chemical composition of the molecules and the number of molecules) and assigning preliminary coordinates to each of the atoms in each molecule. Initial conditions (e.g., temperature, volume, and pressure)

are also set. Temperature and pressure may be set to values that are approximately the same as those in a laboratory, e.g., temperatures in a range from about 20° C. to 50° C., and pressures at about 1 atm. Boundary conditions (e.g., periodic boundary conditions, hard wall boundaries) for the simulation space are also established. Conventional techniques for MD simulations may be used for this purpose.

Establishing the initial system can include equilibrating the aggregate prior to introducing the solvent. For example, once starting parameters for the system are defined, minimization and/or molecular dynamics simulations can be run on the system in order to equilibrate the system. Minimization may be run for one or several thousand steps (e.g., 2,000 steps). In some embodiments, multiple consecutive processes are run. For example, in certain embodiments, multiple MD simulations are run, each under different conditions. For instance, a constant volume MD simulation may be performed, followed by a constant pressure MD simulation.

The length of the MD simulations can vary. Generally, the simulations are run for an amount of time sufficient to adequately equilibrate. In some embodiments, the simulation is run for 0.1 ns to 100 ns.

After initial equilibration, the aggregate is placed in a fixed volume with solvent molecules. The box volume is selected to be larger than the aggregate, providing some buffer between the aggregate and the volume boundaries. For example, a buffer length from about 0.5 nm to about 5 nm may be specified. In some embodiments, the hard wall boundary conditions are selected, in contrast to periodic boundary conditions for example.

In general, the form of the solvent molecules may vary. In some embodiments, solvent molecules are treated as spheres. Alternatively, more complex molecular structure for the solvent molecules may be specified.

The number of solvent molecules may vary and may be selected so that the density of the solvent is correct (i.e., corresponds to the density of the actual solvent) at the specified temperature and pressure. So depending on how the buffer is set, more of fewer solvent molecules are included as appropriate to maintain the correct liquid density for the selected solvent. Alternatively, or additionally, a barostat may be employed during the calculation such that appropriate liquid densities will be achieved during the simulations.

After placing the aggregate in the solvent, the system may again be equilibrated, e.g., using MD simulation.

In step 220, a final state for the system is established. The final state is composed of a transformed version of the aggregate (described below) in the solvent volume along with a single molecule of the compound fully solvated in the solvent and separate from the transformed aggregate.

In a further step 230, using the computer model, the algorithm transforms the system from the initial state to the final state by removing a molecule of the compound from the aggregate and replacing the molecule with solvent molecules at the site of the removed molecule. The removed molecule is removed to vacuum. The remaining aggregate corresponds to the transformed aggregate described in step 220 above. Another molecule of the compound is introduced into the solvent so that the other molecule is fully solvated in the solvent, thereby completing the transformation to final state.

In step 240, the algorithm calculates the free energy of the transformation between the initial and the final states. In some embodiments, this calculation is performed using Free Energy Perturbation. Publicly-available software (e.g., FEP+, from Schrödinger) may be used for performing the calculation.

Other calculation techniques are also possible. For example, in some embodiments, the free energies are calculated by thermodynamic integration. Alternatively, or additionally, the free energies are calculated by determining a potential of mean force. In some embodiments, the free energy of the transformation is determined using the Bennett acceptance ratio (BAR) method.

Calculating the free energy of solubility for the compound may involve repeating steps (ii), (iii) and (iv) for molecules from multiple different sites in the aggregate, and calculating an average of the free energy of transformation from the initial to each of the final state.

The free energy of solubility for the compound is then determined from the free energy of the transformation from the initial state to the final state. This is performed by adding the computed sublimation and solvation free energies, and then converting the solubility free energy to the appropriate units. Solubility may be determined using the formula provided above.

The calculated free energy of solubility may be analyzed in a variety of ways to provide insight into the solubility of the compound. For example, the calculated free energy may be used to calculate a solubility for the compound, e.g., using the equation set forth above. The calculated solubility can be compared to empirical solubility data for the same or similar compounds.

Information about solubility may be gleaned from the solubility free energy itself. For example, comparisons of the free energy values of similar but not identical compounds may reveal which of those compounds have higher solubility relative to others. Such comparisons may aid prioritization of the synthesis of certain variants based on whether the predicted solubility is sufficiently high.

The value of the free energy of solubility may also provide insight into whether a compound is sufficiently soluble. In general, for pharmaceutical use, the thresholds may be determined according to Food & Drug Administration's Biopharmaceutics Classification System (BCS) classification scheme or by the requirements of a particular pharmaceutical program in the pre-formulation stage. Accordingly, comparing the calculated free energy of solubility to this threshold value allows one to identify candidates having satisfactory solubility from unsatisfactory ones.

Figure 3:
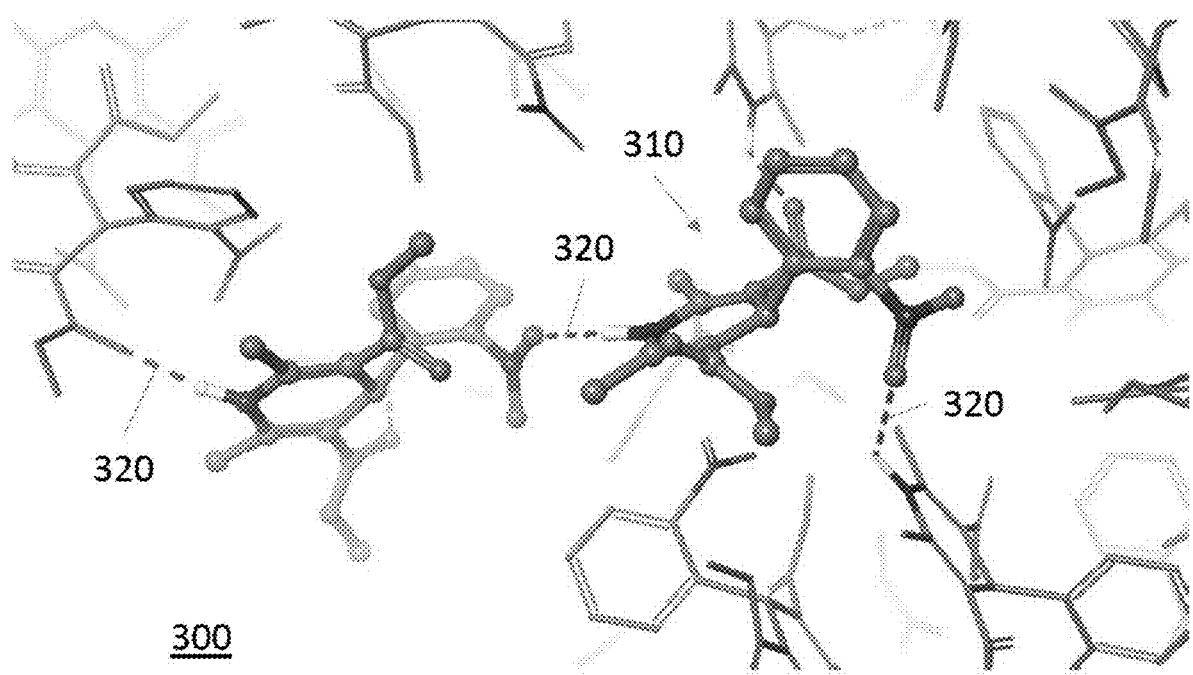
FIG. 3 is a visualization of an aggregate of nifedipine molecules.

In addition, using calculations of solubility free energy alongside visualizations of the corresponding aggregate can provide valuable physical insights into solubility. For example, FIG. 3 shows a computer visualization of an aggregate 300 of nifedipine molecules 310. Nitro groups in neighboring molecules appear to be involved in a polar interaction network 320. It is believed that interactions such as these, which are apparent in the visualization, may result in a larger sublimation free energy for nifedipine compared to, for example, felodipine, which has a similar molecular structure but a smaller sublimation free energy.

Figure 4:
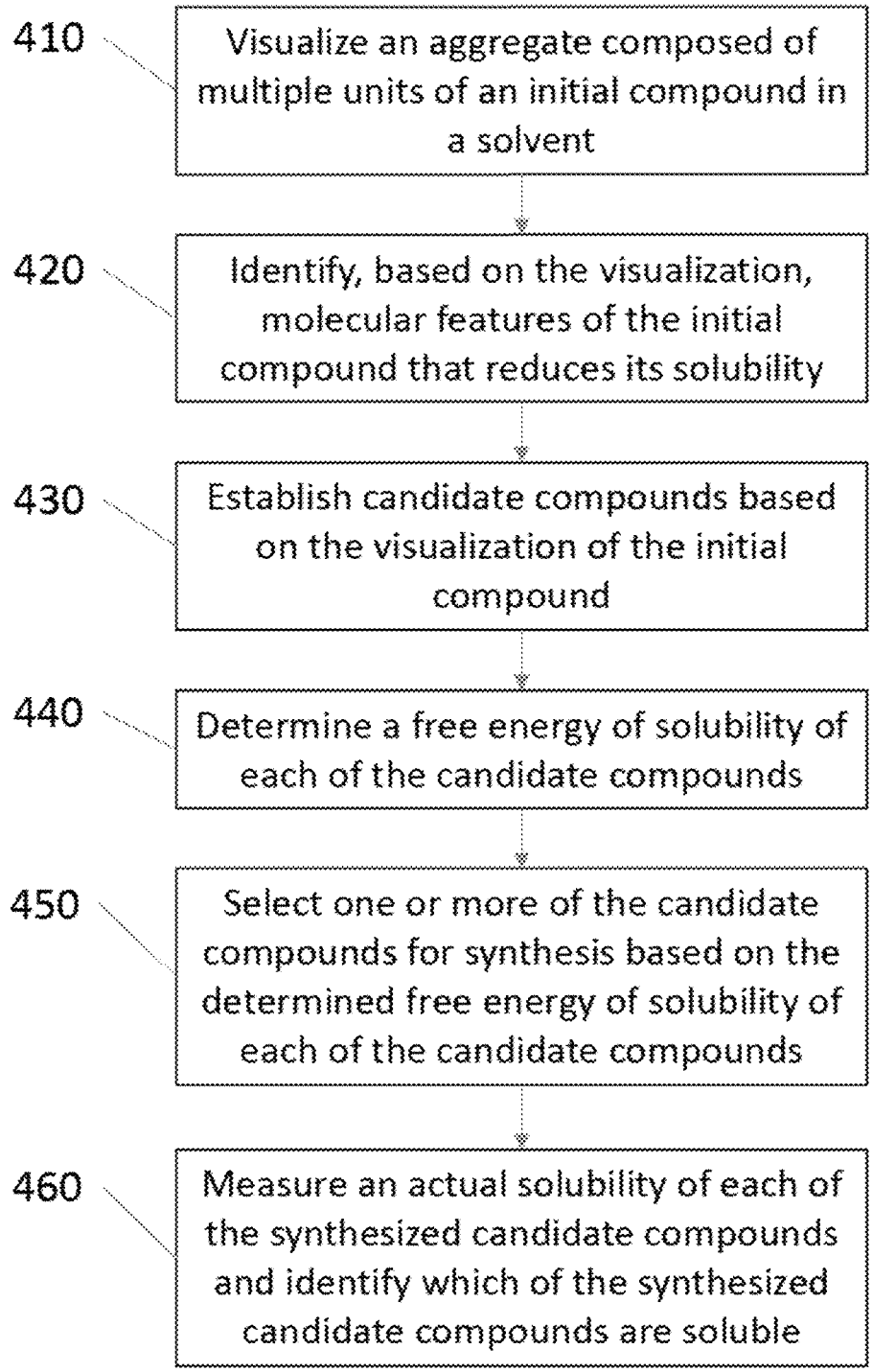
FIG. 4 is a flow chart showing steps in an exemplary rational drug design method that incorporates a calculation of solubility free energy.

The described methods can be used in structure-based design strategies to improve solubility of compounds, such as NMEs. For example, FIG. 4 shows a flow chart illustrating an algorithm (400) for designing soluble compounds that utilizes the above methods for calculating solubility free energy. This involves the step of visualizing, using a computer model, an aggregate composed of multiple units of a compound (the initial compound). The aggregate can be visualized on its own or in the presence of a solvent in which the initial compound is known to be insoluble.

The next step is to identify molecular features of the initial compound that reduces its solubility based on the visualization of the aggregate in the solvent (step 420). To use the example of nefidipine shown in FIG. 3 which suggests that the aggregate has a relatively higher sublimation free energy due to stabilization from polar interaction networks involve a nitro group in the molecule, this step may involve identifying interactions between certain groups in the initial compound that may stabilize the aggregate relative to alternatives.

Different candidate compounds are established based on the visualization of the initial compound (step 430). The structure of each of these candidate compounds is a variant of the initial compound. For instance, one or more groups on the molecule—such as the nitro group in nifedipine—may be substituted with another group. Ideally, the substitution does not worsen the initial compounds suitability for its intended purpose (e.g, its ability to favorably interact with certain receptor molecules), but nevertheless improves the molecules solubility.

Next, a free energy of solubility is determined for each of the candidate compounds (step 440). This step is performed using the methods described above. After determining solubility free energies, one or more of the candidate compounds is selected for synthesis based on the determined free energy of solubility (step 450). Once synthesized, an actual solubility of each of the synthesized candidate compounds is empirically measured and soluble compounds are identified (step 460).

Example 1

An initial disordered system was formed with 64 molecules of felodipine. The system was equilibrated with 2000 steps of minimization, followed by 0.5 ns of NVT MD simulation, and finally 5 ns of NPT MD simulation. The simulations were performed under periodic boundary conditions, at the temperature of interest (37° C. body temperature in this particular case) and pressure of 1 atm for the NPT leg.

The equilibrated aggregate (without its periodic images) was then placed in a water box of 10 Å buffer length, and further equilibrated with 2000 steps of minimization, 0.5 ns of NVT MD simulation, and 5 ns of NPT MD simulation.

The aggregate of ligands was isolated from the last frame of the simulation, and used as the input for the free energy calculation. One molecule of ligand was selected on the surface by computer algorithm, such that its heavy atoms are at least partially exposed to the solvent.

Starting from this input structure, a FEP calculation was performed to alchemically transfer the selected molecule from the aggregate to the vacuum. Although these calculations were for the sublimation free energy, the FEP calculation was carried out with the aggregate in a water bath—this allowed the fast-diffusing water molecules to rapidly replace the ligand being annihilated, and heal the aggregate.

The alchemical procedure was performed for five different surface molecules starting from the same input structure, so as to take into account the heterogeneity of the surface and statistical error. The sublimation free energy was obtained by an averaging procedure, specifically as the median of the five free energy values.

An individual ligand was also transferred alchemically from vacuum to a fully solvated state, to calculate the hydration free energy.

The net free energy of transferring a molecule from the aggregate to the fully solvated state was obtained as the sum of the sublimation and hydration free energies.

For felodipine, the sublimation free energy was computed to be 19 kcal/mol and the hydration free energy to be −12.1 kcal/mol, at 37° C. The net free energy of solubility is 6.9 kcal/mol, which translates to a computed solubility of 8.6 µM. This compares well with experimental measurements (see, e.g., Ilevbare and Taylor 2013) of 2.5 µM "equilibrium" solubility and 22.1 µM "amorphous" solubility. Both computational and experimental data correspond to low solubility (BCS Class II/IV).

Example 2

An initial disordered system was formed with 64 molecules of acetaminophen, which is an analgesic and the active ingredient in medicines like Tylenol. The system was equilibrated with 2000 steps of minimization, followed by 0.5 ns of NVT MD simulation, and finally 5 ns of NPT MD simulation. The simulations were performed under periodic boundary conditions, at room temperature (25° C.) and pressure of 1 atm for the NPT leg.

The equilibrated aggregate (without its periodic images) was then placed in a chloroform box of 10 Å buffer length, and further equilibrated with 2000 steps of minimization, 0.5 ns of NVT MD simulation, and 5 ns of NPT MD simulation.

The aggregate of ligands were isolated from the last frame of the simulation, and used as the input for the free energy calculation. One molecule of ligand was algorithmically selected on the surface, such that its heavy atoms are at least partially exposed to the solvent.

Starting from this input structure, a FEP calculation was performed to alchemically transfer the selected molecule from the aggregate to the vacuum. Although these calculations were for the sublimation free energy, the FEP calculation was carried out with the aggregate in a chloroform bath—this allowed the fast-diffusing chloroform molecules to rapidly replace the ligand being annihilated, and heal the aggregate.

The alchemical procedure was performed for five different surface molecules starting from the same input structure, so as to take into account the heterogeneity of the surface and statistical error. The sublimation free energy was obtained by an averaging procedure, specifically as the median of the five free energy values.

An individual ligand was also transferred alchemically from vacuum to a fully solvated state in water, to calculate the hydration free energy.

The net free energy of transferring a molecule from the aggregate to the fully solvated state was obtained as the sum of the sublimation and hydration free energies.

For acetaminophen, the sublimation free energy was computed to be 17.4 kcal/mol and the hydration free energy to be −15.5 kcal/mol, at 25° C. The net free energy of aqueous solubility is 1.9 kcal/mol, which translates to a computed solubility of 40,000 µM. This compares well with experimental measurement of 14000 mg/L (or ~36,000 µM) aqueous solubility reported in the NIH Pubchem database (https://pubchem.ncbi.nlm.nih.gov/compound/acetaminophen#section=MeSH-Synonyms). Both calculations and experimental measurements correspond to a high aqueous solubility (BCS Class I/III).

Figure 5:
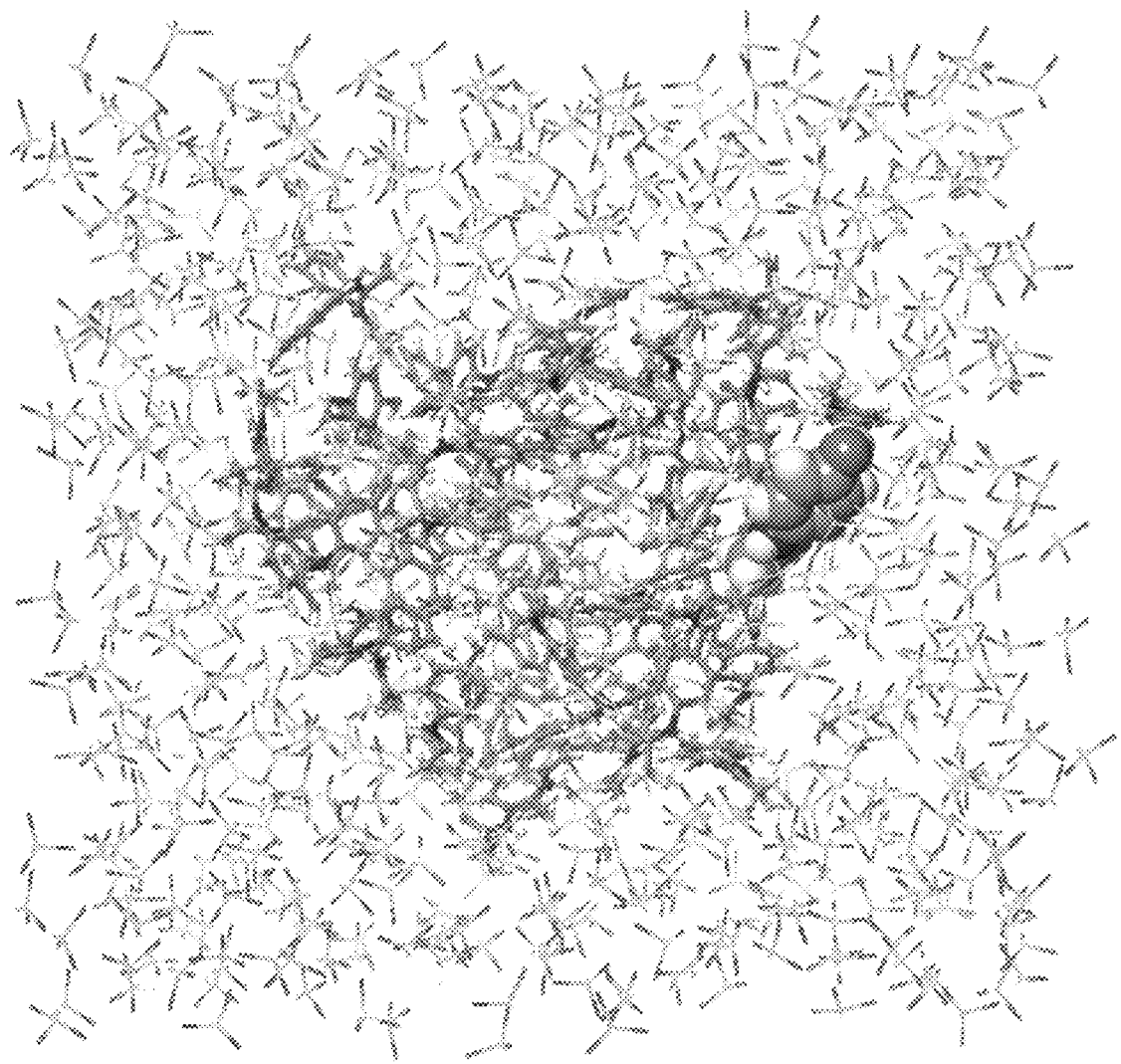
FIG. 5 shows a snapshot from a free energy perturbation to compute acetaminophen sublimation, where Chloroform is used as the fast-diffusing solvent.

FIG. 5 shows a snapshot from a free energy perturbation to compute acetaminophen sublimation, where chloroform is used as the fast-diffusing solvent. The molecule of acetaminophen being annihilated in this particular perturbation is highlighted in Van der Waals.

In addition to examples 1 and 2, the solubilities of a number of exemplary molecules are tabulated below in Table 1 and compared against their respective experimentally determined solubilities. The solubilities were computed using the methods described above for example 1, using the solvent and temperature at which the experimental solubilities were measured.

TABLE 1

| Compound | Expt. Solubility (μM) | Comp. Solubility (μM) |
|---|---|---|
| clotrimazole | 1.16 | 16.91 |
| clozapine | 26.93 | 44.81 |
| indomethacin | 8.38 | 27.07 |
| ritonavir | 1.80 | 0.13 |
| loratadine | 4.18 | 3.35 |
| glipizide | 9.20 | 13.65 |
| danazol | 0.89 | 0.60 |

In general, implementations of the methods described above may be implemented as computer software products for use with computer systems. Such programs may be contained on a variety of signal-bearing media. Examples of signal-bearing media include (i) information permanently stored on non-writable storage media (e.g., a CD or DVD disk); (ii) alterable information stored on writable storage media (e.g., floppy disks within a diskette drive or hard-disk drive); and (iii) information conveyed to a computer by a communications network, including wireless communications. The latter specifically includes information made available on the Internet and other networks. Such signal-bearing media, carrying computer-readable instructions that implement the methods of the invention, represent embodiments of the invention.

Embodiments may be implemented using any available computer system and adaptations are contemplated for both known and later developed computing platforms and hardware. Accordingly, the methods described may be carried out by software applications configured to execute on computer systems ranging from single-user workstations, client server networks, large distributed systems employing peer-to-peer techniques, or clustered grid systems. Further, computer systems used to practice the methods may be geographically dispersed across local or national boundaries using a network. Moreover, data generated for a molecule at one location may be transported to other locations using well-known data storage and transmission techniques, and predictions may be verified experimentally at the other locations. For example, a computer system may be located in one country and configured to generate predictions about the property of interest for a selected group of molecules, this data may then be transported (or transmitted) to another location, or even another country, where it may be the subject of further investigation e.g., laboratory confirmation of the prediction or further computer-based simulations.

A number of embodiments have been described. Nevertheless, it will be understood that various modifications may be made without departing from the spirit and scope of the invention. Accordingly, other embodiments are in the following claims.

What is claimed is:

1. A computer-implemented method for screening compounds for solubility in a solvent, the method comprising:
   identifying a plurality of different candidate compounds each based on an initial compound, a structure of each of the candidate compounds being variants of the initial compound;
   calculating a free energy of solubility of each of the candidate compounds in the solvent according to the following steps:
   (i) establishing, using a computer model, an initial state for a system comprising an aggregate of multiple molecules of the candidate compound in a solvent;
   (ii) establishing, using the computer model, a final state of the system comprising a single molecule from the aggregate fully solvated in the solvent and separate from a transformed aggregate;
   (iii) transforming, using the computer model, the system from the initial state to the final state, via removing a first molecule of the compound from the aggregate to form the transformed aggregate and replacing the first molecule with solvent at the site of the first molecule; and
   (iv) calculating the free energy of the transformation between the initial and the final states, which determines the free energy of solubility for the compound in the solvent; and
   synthesizing at least one of the candidate compounds based on the calculated free energy of solubility of each of the candidate compounds.

2. The method of claim 1, wherein the aggregate is an amorphous solid.

3. The method of claim 1, wherein the aggregate is a crystal.

4. The method of claim 1, wherein the aggregate is a super-cooled liquid.

5. The method of claim 1, wherein transforming the initial state to the final state comprises the steps of:
   (i) removing a first molecule of the compound from the aggregate to vacuum, and replacing the first molecule with solvent at the site of the first molecule; and
   (ii) introducing a second molecule of the compound into the solvent so that the second molecule is fully solvated in the solvent.

6. The method of claim 1, wherein the free energies are calculated via free energy perturbation.

7. The method of claim 1, wherein the free energies are calculated by thermodynamic integration.

8. The method of claim 1, wherein the free energies are calculated by determining a potential of mean force.

9. The method of claim 1, wherein the free energies are calculated by Bennett acceptance ratio (BAR) method.

10. The method of claim 1, wherein the free energies are calculated by Zwanzig averaging.

11. The method of claim 1, wherein the first unit is located at an interface between the aggregate and the solvent.

12. The method of claim 1, wherein calculating the free energy of solubility for the compound comprises repeating steps (ii), (iii) and (iv) for molecules from multiple different sites, and calculating an average of the free energy of initial and final states of the system for the multiple different sites.

13. The method of claim 1, wherein establishing the initial system comprises equilibrating the aggregate and then introducing the aggregate into the solvent and equilibrating the aggregate in the solvent.

14. The method of claim 1, wherein system is simulated using Molecular Dynamics or Monte Carlo simulations.

15. The method of claim 1, wherein the solvent is water.

16. The method of claim 1, wherein the compound is a small molecule.

17. The method of claim 1, further comprising designing a new compound based on visualizing the aggregate in the solvent.

18. The method of claim 17, wherein the small molecule is a candidate molecule for a pharmaceutical application.

19. The method of claim 1, wherein the initial compound is insoluble in the solvent.

20. A system for screening compounds for solubility in a solvent, the system comprising:
one or more computers programmed to execute instructions to:
receive information about a plurality of different candidate compounds each based on an initial compound, a structure of each of the candidate compounds being variants of the initial compound;
calculate a free energy of solubility of each of the candidate compounds in the solvent according to the following steps:
(i) establishing, using a computer model, an initial state for a system comprising an aggregate of multiple molecules of the candidate compound in a solvent;
(ii) establishing, using the computer model, a final state of the system comprising a single molecule from the aggregate fully solvated in the solvent and separate from a transformed aggregate;
(iii) transforming, using the computer model, the system from the initial state to the final state, via removing a first molecule of the compound from the aggregate to form the transformed aggregate and replacing the first molecule with solvent at the site of the first molecule; and
(iv) calculating the free energy of the transformation between the initial and the final states, which determines the free energy of solubility for the compound in the solvent; and
output information about the solubility of each of the candidate compounds in the solvent.

21. A non-transitory computer readable medium containing program instructions for screening compounds for solubility in a solvent, wherein execution of the program instructions by one or more processors of a computer system causes the one or more processors to carryout the steps of: identifying a plurality of different candidate compounds each based on an initial compound, a structure of each of the candidate compounds being variants of the initial compound; calculating a free energy of solubility of each of the candidate compounds in the solvent according to the following steps: (i) establishing, using a computer model, an initial state for a system comprising an aggregate of multiple molecules of the candidate compound in a solvent; :Feb. 4, 2019: 6 of 11(ii) establishing, using the computer model, a final state of the system comprising a single molecule from the aggregate fully solvated in the solvent and separate from a transformed aggregate; (iii) transforming, using the computer model, the system from the initial state to the final state, via removing a first molecule of the compound from the aggregate to form the transformed aggregate and replacing the first molecule with solvent at the site of the first molecule; and (iv) calculating the free energy of the transformation between the initial and the final states, which determines the free energy of solubility for the compound in the solvent; and synthesizing at least one of the candidate compounds based on the calculated free energy of solubility of each of the candidate compounds.

* * * * *

UNITED STATES PATENT AND TRADEMARK OFFICE
CERTIFICATE OF CORRECTION

PATENT NO. : 10,783,985 B2  
APPLICATION NO. : 16/267085  
DATED : September 22, 2020  
INVENTOR(S) : Mondal et al.

Page 1 of 1

It is certified that error appears in the above-identified patent and that said Letters Patent is hereby corrected as shown below:

In the Claims

Column 14, Line 18, in Claim 21, after "solvent;" delete ":Feb. 4, 2019: 6 of 11".

Signed and Sealed this  
Twenty-ninth Day of December, 2020

Andrei Iancu  
*Director of the United States Patent and Trademark Office*